(12) United States Patent
Favre-Bulle et al.

(10) Patent No.: US 6,180,359 B1
(45) Date of Patent: Jan. 30, 2001

(54) INDUSTRIAL SCALE PROCESS FOR THE PREPARATION OF 2-HYDROXY-4-METHYLBUTYRIC ACID USING A NITRILASE

(75) Inventors: Olivier Favre-Bulle; Jérôme Pierrard; Christophe David, all of Lyons; Philippe Morel, Chuzelles; Dominique Horbez, Franconville, all of (FR)

(73) Assignee: Aventis Animal Nutrition S.A., Antony Cedex (FR)

( * ) Notice: Under 35 U.S.C. 154(b), the term of this patent shall be extended for 0 days.

(21) Appl. No.: 08/957,621

(22) Filed: Oct. 24, 1997

(30) Foreign Application Priority Data

Oct. 25, 1996 (FR) .................................................. 96 13077

(51) Int. Cl.$^7$ ................................ C12P 1/00; C12P 7/40; C12N 9/00; C12N 9/78
(52) U.S. Cl. ........................... 435/41; 435/136; 435/174; 435/183; 435/227
(58) Field of Search .................................. 435/136, 174, 435/41, 183, 227

(56) References Cited

U.S. PATENT DOCUMENTS

| | | | | |
|---|---|---|---|---|
| 4,732,851 | * | 3/1988 | Wood et al. ........................... | 435/43 |
| 4,800,162 | * | 1/1989 | Matson .................................. | 435/280 |
| 5,629,190 | * | 5/1997 | Petre et al. ........................... | 435/227 |
| 5,814,497 | * | 9/1998 | Favre-Bulle et al. ................ | 435/130 |

FOREIGN PATENT DOCUMENTS

| | | | |
|---|---|---|---|
| 0 089 165 | 9/1983 | (EP) | ..................................... 435/181 |
| 0 206 687 | 12/1986 | (EP) | ..................................... 435/181 |
| 0 237 620 | 9/1987 | (EP) | ..................................... 435/136 |
| 0 731 079 | 9/1996 | (EP) | ..................................... 435/130 |
| 53-056385 | 5/1978 | (JP) | ..................................... 435/177 |
| WO 91/08287 | 6/1991 | (WO) | ....................................... 435/94 |
| WO 96/09403 | 3/1996 | (WO) | ..................................... 435/139 |

OTHER PUBLICATIONS

Bio–Rad Catalog, Life Science Research Products, pp. 6–7, 1993.*
Chibata, I., Immobilized Enzymes, Research and Development, pp. 11–13, 1978.*
M. Kobayashi et al. Proceedings of the National Academy of Sciences of USA, vol. 90, No. 1, pp. 247–251, Jan. 1, 1993.
French Search Report for FR application 9613077, 1997.

* cited by examiner

Primary Examiner—Karen Cochrane Carlson
Assistant Examiner—Holly Schnizer
(74) Attorney, Agent, or Firm—Finnegan, Henderson, Farabow, Garrett, & Dunner, L.L.P.

(57) ABSTRACT

This invention relates to a process for the preparation of 2-hydroxy-4-methylthiobutyric acid or the ammonium salt of 2-hydroxy-4-methylthiobutyric acid by enzymatic hydrolysis of 2-hydroxy-4-methylthiobutyronitrile, comprising:

a) preparing a biological material having a nitrilase activity;

b) immobilizing the biological material, c) exposing the 2-hydroxy-4-methylthiobutyronitrile to the biological material thus immobilized to obtain the ammonium salt of 2-hydroxy-4-methylthiobutyric acid; and d) optionally converting the salt obtained to the corresponding acid.

24 Claims, 7 Drawing Sheets

INDUSTRIAL SCALE PROCESS FOR THE PREPARATION OF 2-HYDROXY-4-METHYLBUTYRIC ACID USING A NITRILASE

FIELD OF THE INVENTION

The present invention relates to a new process for the preparation of 2-hydroxy-4-(methylthio)butanoic acid (HMTBA) and/or its ammonium salt (HMTBS).

BACKGROUND OF THE INVENTION

2-Hydroxy-4-methylthiobutyric acid and its salts have been used for a long time in animal nutrition as a replacement for methionine because they have the advantage of having a liquid form, which facilitates their use by feed producing companies.

The preparation of 2-hydroxy-4-(methylthio)butanoic acid by a chemical route has been known for a long time. European patent nos. EP-142 488 and 143 000 describe the hydrolysis of 2-hydroxy-4-methylthio-hydroxybutyronitrile (HMTBN) by a two-stage process. The first stage consists in bringing the 2-hydroxy-4-methylthiobutyronitrile into contact with a strong inorganic acid such as hydrochloric or sulphuric acid. In a subsequent stage, after dilution with water, the hydrolysis is completed at a higher temperature. The 2-hydroxy-4-(methylthio)butanoic acid is then extracted with an organic solvent which is not very miscible with water, such as a ketone, preferably methyl isobutyl ketone, and then the solvent is removed by evaporation. This type of process, which is used industrially, nevertheless has some disadvantages. In particular, it produces a molar quantity of ammonium sulphate, at least equal to the molar quantity of nitrile introduced, which has to be removed, thus generating an industrial waste which runs counter to environmental protection policies. This process also requires the use of large quantities of solvent which must be recycled.

Other processes such as those described in U.S. Pat. No. 3,773,927 and 4,353,924 consist in hydrolysing 2-hydroxy-4-methylthio-butyronitrile with hydrochloric acid and then concentrating the medium with separation of the ammonium chloride formed. The salt obtained is as difficult to remove as the preceding salt and, furthermore, the acid obtained has a strong color.

A process for the chemical hydrolysis of methylthio-hydroxypropionitrile which consists, as above, in carrying out a hydrolysis in a sulphuric medium, is described in European Patent No. 330 521. The mixture is partially neutralized with ammonium hydroxide followed by a two-phase separation. The organic phase contains most of the 2-hydroxy-4-methylthiobutyric acid and the aqueous phase contains most of the ammonium sulphate produced. The organic solution, after evaporation of the water which it contains, is filtered so as to recover the dissolved ammonium sulphate. The 2-hydroxy-4-methylthiobutyric acid is then diluted with a small quantity of water and stabilized with a small quantity of sulphuric acid. The aqueous solution, after elimination of the water, makes it possible to obtain ammonium sulphate which is directly marketable. This process partly overcomes the disadvantages of the prior art process with regard to the use of organic solvents, but does not in any way solve the problems linked to the discharge of the inorganic salts.

Among the patents relating to the salts of 2-hydroxy-4-methylthiobutyric acid, there may be mentioned U.S. Pat. Nos. 2,745,745, 2,938,053, and 3,175,000, which relate to calcium and/or ammonium salts. The mixture obtained by hydrolysis of the 2-hydroxy-4-methylthiobutyronitrile is treated with calcium hydroxide or carbonate. The calcium sulphate is then precipitated, releasing the ammonium hydroxide which forms the ammonium salt of 2-hydroxy-4-methylthiobutyric acid. Here again, the problem consists in removing the calcium sulphate which remains.

A process which consists in carrying out a hydrolysis and an extraction with an organic solvent, as in the first document cited above, followed by a neutralization of the organic solution with ammonium hydroxide is also described in International Patent Application WO 96/01808. This process, as in the majority of the processes previously described, leads to the formation of at least one mole of ammonium sulphate or chloride per mole of nitrile introduced and requires the recycling of large quantities of organic solvent. Thus, it is not possible to obtain a solution of ammonium salt of 2-hydroxy-4-methylthiobutyric acid at an industrially advantageous cost.

The use of a nitrilase as a catalyst for the hydrolysis of a nitrile group into a carboxyl group is disclosed in U.S. patent application Ser. No. 08/809,184, filed Mar. 20, 1997 now U.S. Pat. No. 5,814,497. This process, however, is not capable of being used on an industrial scale given the insufficient activity of the microorganisms which synthesize these nitrilases.

SUMMARY OF THE INVENTION

It has now been discovered, by virtue of the process of this invention, that by using several specific stages, it is possible to obtain 2-hydroxy-4-methylthiobutanoic acid and/or its ammonium salt by an enzymatic route on an industrial scale, with a high yield, without the use of solvents and without the concomitant production of inorganic salts.

A subject of the invention is thus a process for the preparation of 2-hydroxy-4-methylthiobutyric acid (HMTBA) and/or of the ammonium salt of 2-hydroxy-4-methylthiobutyric acid (HMTBS) by enzymatic hydrolysis of 2-hydroxy-4-methylthiobutyronitrile, characterized in that:

a) in a first stage, a biological material having a nitrilase activity is prepared, b) in a second stage, the biological material is immobilized, c) in a third stage, the 2-hydroxy4-methylthiobutyronitrile is exposed to the immobilized biological material in order to obtain the ammonium salt of 2-hydroxy-4-methylthiobutyric acid, d) in a fourth stage, the salt obtained in c) is optionally converted to the corresponding acid, and e) in a fifth stage, the product obtained in c) or d) is concentrated.

DESCRIPTION OF THE DRAWINGS

The invention will be explained in greater detail in the following description for which reference will be made to the accompanying Figures.

FIG. 1 represents a schematic representation of an electrodialysis cell used in the optional stage d);

DETAILED DESCRIPTION OF THE INVENTION

Figure 1A:
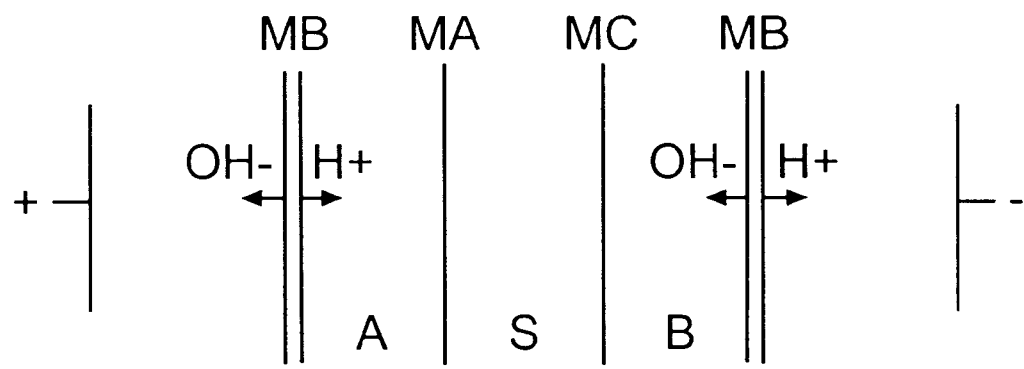
FIG. 1A represents an electrodialysis cell with a bipolar membrane having three compartments.

The first stage in the process of preparing 2-hydroxy4-methylthiobutanoic acid comprises preparing a biological material having a nitralase activity. The biological material may contain an enzymatic solution as such or whole or broken cells having a nitrilase activity.

Advantageously, a nitrilase-expressing microorganism is used. The nitrilase may be derived especially from a microorganism, in particular a microorganism of the genus Alcaligenes, Rhodococcus or Gordona, preferably, *Alcaligenes faecalis*, Rhodococcus sp. HT 29-7, *Gordona terrae*, and more preferably, the strains described in U.S. patent application Ser. No. 08/809,184 now U.S. Pat. No. 5,814,497.

Advantageously, a microorganism is used which expresses a nitrilase activity obtained by transferring the genetic information encoding the nitrilase of a parental microorganism into a host microorganism. In particular, in *E. col*, it is possible to use the coexpression of the chaperon proteins Gro ESL to enhance the performance of the recombinant strain. To this end, any appropriate expression vector, in particular a plasmid vector, is used.

The nucleotide sequence used in this case will then be placed under the control of signals allowing its expression in a cell host. The cell host used may be chosen from prokaryotic systems, such as Gram-positive or Gram-negative bacteria, or eukaryotic systems, such as, for example, yeast, fungi or any other system. The signals controlling the expression of the polypeptides are chosen according to the cell host used. To this end, the DNA encoding a nitrilase may be inserted into autonomously replicating vectors inside the chosen host or integrative vectors of the chosen host. Such vectors will be prepared according to methods commonly used by persons skilled in the art, and the resulting constructs may be introduced into an appropriate host by standard methods such as electroporation.

By way of host microorganisms, there may be mentioned in particular *Alcaligenes faecalis, Pseudomonas putida, Escherichia coli*, or microorganisms of the genii Bacillus, Corynebacterium, Streptomyces, Saccharomyces, Kluyveromyces, Penicillium and Aspergillus.

A preferred vector for the expression in *E. coli* is the plasmid pRPA-BCAT6.

The second stage of the process comprises immobilizing the biological material. This immobilization is advantageously performed in the presence of a solid support, and makes it possible to obtain solid particles whose size, shape and mechanical resistance can be controlled. It also allows the simultaneous use of polyazetidine polymer and other cross-linking agents.

This immobilization process may involve whole cells or cells which have been made permeable. It may also apply to a cell-free enzymatic solution. The enzymes used for the immobilization are the nitrilases.

The immobilization process comprises immobilizing the active biological material on a solid support, especially with a particle size of between 1 µm and 500 µm, preferably 10 µm and 200 µm, by means of chemical agents which react with the amine ($NH_2$, NH), carboxyl (COOH), hydroxyl (OH), thiol (SH) or amide ($CONH_2$) functional groups of the biological agent and of the support. These chemical agents also make it possible to insolubilize the biological material and the support in water. The mass obtained is very malleable and may be shaped in order to obtain particles of desired shape and size. The cohesion and hardness of these particles are then obtained by drying.

The biological material to be immobilized may optionally also contain an inactive biological material present in an amount of 0 to 200% by weight. This inactive biological material may be proteins (albumin or gelatin) or polysaccharides (Chitosan, k-carrageenan, or alginate).

The inert support on which the biological material is deposited and the polymer may be composed of hydrophilic or hydrophobic, porous or nonporous, organic or inorganic particles. Among these particles, there may be mentioned, with no limitation being implied, ion-exchange resins, alumina, synthetic silicas or diatomaceous earth and silica gels, zeolites, charcoals, water-insoluble proteins such as gluten, and polysaccharides such as starch.

The inert support may be added in an amount of 0.01 to 200% by weight of biological material, and preferably 10 to 100%.

The chemical agents used to insolubilize the biological material may be polymers or bifunctionalized molecules which react with the amine ($NH_2$, NH), carboxyl (COOH), hydroxyl (OH), thiol (SH) or amide ($CONH_2$) functional groups. There may be mentioned polyazetidine polymers, polyethyleneimine polymers, polyamide polymers, isocyanate polymers, alginate gels, k-carrageenan gels, amines such as hexamethylenediamine, aldehydes such as glutaraldehyde, carboxylic acids such as adipic acid, and isocyanates.

The immobilization process may involve one or more of these chemical agents. The chemical agent is added in a concentration of between 1 and 50% by weight relative to the biological material and to the support. A quantity of between 5 and 30% will be preferred in order to obtain sufficiently solid particles which conserve a high activity and that do not have too many problems of internal diffusion.

The duration of a cross-linking treatment is between 0.5 and 24 hours.

The process temperature is generally between 4 and 65° C. A temperature of between 20 and 40° C. is preferred. The temperature used during the immobilization process may also be highly dependent on the stability of the biological material used.

The pH during the immobilization phase is maintained between 5 and 11. A pH of between 6 and 10 is preferred, with a preference for alkaline pH values. The pH is also chosen as a function of the resistance of the biological material and is easily determined by persons skilled in the art.

The forming of the biocatalyst should allow its use in any system, especially in a fixed bed.

One formulation method may be extrusion. To do this, the biological material and the support are cross-linked by adding one or more chemical agents. After treatment, the insoluble mass is recovered by centrifugation or by flocculation and filtration. A dry matter level of at least 10% is preferred. The mass is then extruded. Using this method, vermicelli with a diameter of between 0.3 and 0.5 mm and a length of between 1 and 10 mm are preferably obtained. These vermicelli may be spheronized. The particles obtained are then dried.

Another formulation method may be spray coating. To do this, the biological material is mixed with one or more chemical agents. After reaction, the mixture is sprayed onto the support in the form of a thin layer. Using this method, granules with a mean diameter of between 0.1 and 2 mm are obtained.

The particles obtained may then be optionally immersed in a solution of a reducing agent, such as sodium borohydride, in order to reduce the imine functional groups formed during the cross-linking.

The particles obtained are sufficiently solid and resistant to attrition to be used in a fixed bed, a fluidized bed, or a stirred reactor.

The third stage of the process according to the invention comprises using the immobilized biological material in one or more columns or reactors. The aim of this stage is to be able to continuously produce the ammonium salt of 2-hydroxy-4-methylthiobutyric acid from 2-hydroxy-4-methylthiobutyronitrile. The column(s) or reactor(s) is(are) supplied with a pure or dilute solution of 2-hydroxy4-methylthiobutyronitrile or a mixture containing 2-hydroxy-4-methylthiobutyronitrile and the ammonium salt of 2-hydroxy-4-methylthiobutyric acid.

The column(s) or reactor(s) is/are preferably used at a temperature of between 10 and 60° C. and at a pH of between 5 and 9.

The system used may include two or more columns connected to each other in series, with, according to a first embodiment of the invention, the supply of the aqueous 2-hydroxy4-methylthio-butyronitrile solution at the top of the first column with a simultaneous supply of the other columns with the 2-hydroxy-4-methylthiobutyronitrile solution in a quantity limited to the solubility of this compound in the reaction mixture. This system is called a staged system.

According to a second embodiment of the invention, one or more columns connected to each other in parallel in a circulation loop are used. According to this plant, the 2-hydroxy-4-methylthiobutyronitrile in aqueous solution is continuously supplied to the loop, and the reaction medium is continuously pumped so as to conserve a constant volume in the loop. This system is called a loop system.

The type of reactor used in this invention may be of the fixed bed, fluidized bed or continuously stirred bed type. The fixed bed-type reactors are preferably used because they reduce the problems of attrition which may be encountered with the immobilized cell particles. If the microorganism is used as it is, a stirred reactor coupled to an ultrafiltration module to continuously separate the microorganism from the product of interest is preferably used.

The fourth stage, which is an optional stage, comprises converting the ammonium salt of 2-hydroxy-4-methylthiobutyric acid to the corresponding acid. This stage may be carried out according to two methods: either by electrodialysis by means of a two- or three-compartment electrodialyzer; or by heating the aqueous solution which may be followed by a liquid/liquid extraction.

Depending on the electrodialysis method, a two- or three-compartment electrodialyzer may be used.

"Compartment" is understood to mean the space which is either between two membranes or between a bipolar and a homopolar membrane, or between two adjacent homopolar membranes. "Cell" is understood to mean a set of two or three compartments. A stack comprises between 5 and 300 cells. The electrodialyser is composed of a stack and of course comprises an anode and a cathode.

The homopolar membranes which may be used within the framework of the invention can be divided into two large families, depending on their mode of manufacture.

Thus, heterogeneous membranes prepared from ion-exchange resins and mixed with a binder such as polyvinyl chloride, polyethylene and the like, may be used. The set thus formed may coat a weft of, for example, a polyester or polyacrylonitrile fabric.

It is also possible to use homogeneous membranes obtained by introducing a functional group onto an inert support by chemical or radiochemical grafting. The most widely used chemical method generally includes functionalizing a latex of a polymer comprising aromatic rings, such as styrene/divinylbenzene or styrene/butadiene. The latex thus functionalized may then serve to coat a weft, similar to the heterogeneous membranes. The radiochemical method generally comprises the grafting, under the influence of a radiation, of an aromatic compound, such as styrene, onto an inert support such as a polyethylene or polytetrafluoroethylene sheet. The aromatic ring is then functionalized as in the chemical method.

The cation-exchange membranes comprise strong acid groups, most often sulphonate groups, or weak acid groups, often carboxylate groups. More rarely, the acidic groups may be $PO_2^{2-}$, $HPO_2^-$, $AsO_3^{2-}$, $SeO_3^-$.

The anion-exchange membranes comprise strong basic groups, most often quaternary ammonium groups, or weak basic groups, most often amine groups. More rarely, the basic groups may be quaternary phosphonium groups or sulphonium groups.

In the present process, the cationic membranes preferably comprise strong acidic groups and among these, preferably sulphonate groups. The anionic membranes preferably comprise strong basic groups and among these, quaternary ammonium groups.

The bipolar membranes are an assembly of two membranes, one cationic, the other anionic. When the membrane is subjected to an adequate electric field, the water of solvation at the interface of the membrane dissociates into $H^+$ and $OH^-$ ions which migrate towards the cathode by crossing the cationic face and towards the anode by crossing the anionic face, respectively. There may be mentioned, by way of example, the bipolar membranes marketed by Aqualytics, Tokuyama Soda or FuMaTech.

The anode of the electrodialyzer may comprise materials conventionally used in electrodialysis, for example, graphite, nickel or titanium coated with precious metals or precious metal oxides, especially platinized titanium. The cathode may also comprise materials conventionally used in electrodialysis, for example, graphite, stainless steel or nickel.

The electrodialyzer is supplied with the aqueous solution to be treated. It is also necessary to circulate to the anode a solution of an anolyte and to the cathode a solution of a catholyte. A single electrolyte solution may also be used. In the present process, a single electrolyte circuit is quite suitable. The role of the electrolyte solution is to ensure a sufficient conductivity. Preferably, this conductivity will be equal to or greater than 20 millisiemens per centimetre (mS/cm), without this lower limit being considered to be critical for carrying out the process.

The electrolyte used is an ionizable compound such as a salt, an acid or a base. The electrolyte is preferably chosen from nonelectroactive compounds. Thus, for example, it is preferable to use neutral salts such as sulphates, acids such as sulphuric acid, and bases such as sodium hydroxide.

The applied current densities generally range from 0.2 to 1.5 $kA/m^2$, and preferably range from 0.4 to 1 $kAm^2$.

The temperature at which the process of the invention is carried out is situated in a range compatible with the stability of the membranes. The procedure will be preferably carried out at a temperature ranging from 30 to 60° C.

The electrodialyzer can work in different ways. It can work continuously, the solution to be treated continuously crossing the stack; several stages are then placed in series if the level of treatment to be obtained requires it. It can also work batchwise, the solution to be treated recirculating over a tank until the desired treatment level is obtained. Finally, it can work by direct passage with partial recirculation.

According to a first variant of the invention, the dissociation of the ammonium salt into 2-hydroxy-4-(methylthio) butanoic acid and ammonium hydroxide can occur in an electrodialysis cell with bipolar membranes having three compartments, as schematically represented in FIG. 1A.

An electrodialysis apparatus suitable for carrying out the process contains different compartments, respectively delimited by cationic membranes (MC), bipolar membranes (MB) and anionic membranes (MA). These compartments divide into a salt compartment (S) which is depleted of compounds to be separated, into a base compartment (B) and an acid compartment (A) where the acid and the base regenerated from the salt are concentrated respectively.

The ammonium salt is introduced into the salt compartment. Under the action of the electric field, the ammonium ion migrates towards the cathode, leaving the compartment (S) where it is present, across a cation-exchange membrane (cationic membrane) and combines with the $OH^-$ ions from the anionic face of the bipolar membrane, in which the dissociation of the water occurs under the effect of the electric field.

Simultaneously, the carboxylate (2-hydroxy-4-(methylthio)butanoate) ions migrate towards the anode, leaving the compartment (S) where they are present, across an anion-exchange membrane (anionic membrane). After passing into the next compartment (A), they are protonated through the supply of $H^+$ ions from the cationic face of the bipolar membrane. The three adjacent compartments (B), (A), and (S) form an electrodialysis cell.

Figure 1B:
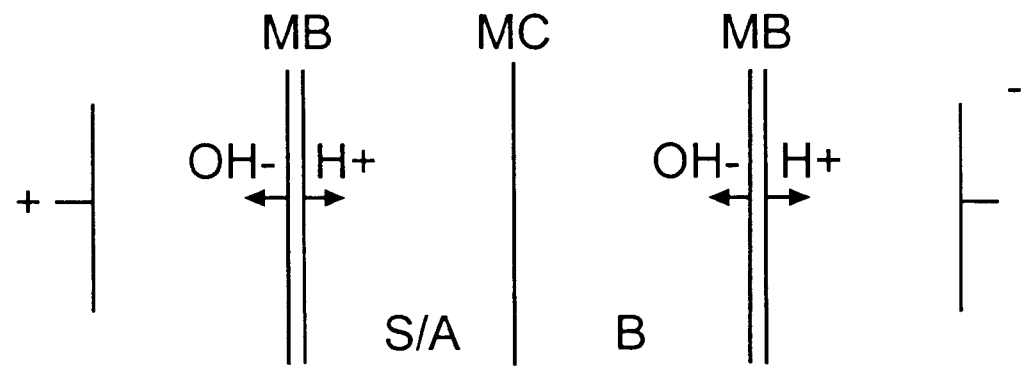
FIG. 1B represents an electrodialysis cell with a bipolar membrane having two compartments.

In a second variant of the invention, the regeneration of the 2-hydroxy-4-(methylthio)butanoic acid can take place in an electrodialysis cell with bipolar membranes having two compartments as represented in FIG. 1B. These two compartments are delimited by cationic membranes and bipolar membranes respectively. These compartments divide into a salt/acid (S/A) and base (B) compartment.

The ammonium salt is introduced into the salt/acid compartment. Under the action of the electric field, the ammonium ion migrates towards the cathode by leaving the compartment (S/A) where it is present, across a cation-exchange membrane (cationic membrane) and combines with the $OH^-$ ions from the anionic face of the bipolar membrane, in which the dissociation of the water occurs under the effect of the electric field.

Simultaneously, the compartment S/A becomes acidified through the supply of $H^+$ ions from the cationic face of the bipolar membrane. The two adjacent compartments (B) and (S/A) form an electrodialysis cell.

This configuration has the advantage of a lower energy consumption and makes it possible to vary the desired salt/acid ratio.

To obtain a good operation of the electrodialyzer, the electrical conductivity of the base compartment (as well as that of the acid compartment in the case of the three-compartment configuration) should be adequate and can be adjusted by addition of a support electrolyte. Thus, the conductivity of the ammonium hydroxide solution may be increased by adding an ammonium salt, such as ammonium sulphate.

In a preferred variant of the invention, ammonium 2-hydroxy-4-methylthiobutanoate is used.

In a preferred embodiment which can be envisaged within the framework of the present invention, a mixture of ammonium salt of 2-hydroxy-4-methylthiobutyric acid and 2-hydroxy-4-methylthiobutyro- nitrile is introduced into the salt compartment of a three-compartment electrodialysis cell. The salt is dissociated as above into 2-hydroxy-4-methylthiobutyrate and migrates towards the anode where it is converted to 2-hydroxy-4-methylthiobutyric acid, the ammonium ion migrates towards the cathode where it is converted to ammonium hydroxide, and there remains in the salt compartment the water and the unconverted 2-hydroxy-4-methylthiobutyronitrile which are recycled towards the hydrolysis column.

Using the heating method, the acid is recovered by shifting the ammonium salt, free acid equilibrium by heating the HMTBS-rich aqueous solution and by withdrawing the ammonium hydroxide thus released. This can be achieved by heating under vacuum or at atmospheric pressure with or without a stripping treatment. The use of $CO_2$ under pressure may be envisaged in order to facilitate the shifting of the equilibrium. A mixture of HMTBS and HMTBA is obtained in an amount of 5 to 99.9% HMTBA, and preferably 10 to 50% HMTBA relative to the sum of HMTBA and HMTBS.

The viscosity of these solutions are between 1200 and 30 mm$^2$·s$^{-1}$ (1200 and 30 cSt) and preferably between 200 and 50 mm$^2$·s$^{-1}$ (200 and 50 cSt) at 25° C.

The aqueous solutions may be decomposed by extraction of the acid with the use of partially water-miscible or water immiscible solvent products. A large number of possible solvents exist for the separation. The preferred solvents are C$_5$ to C$_8$ ketones, in particular methyl isobutyl ketone, esters such as isopropylether, alcohols such as isopropanol, esters, tertiary amines such as trioctylamine. Within the framework of the invention, the preferred solvents are: acetone, MIBK, isopropanol, isopropyl acetate, isobutyl or propyl ether, THF, or trioctylamine. The ratio of the aqueous phase to the organic phase is not critical. However, for reasons of degree of efficacy, it should not fall below a minimum ratio of 1:1 and for reasons of profitability, it should not rise above a ratio of 1:3. A 1:1.5 to 2.0 ratio is preferred.

The extraction may be carried out batchwise or continuously, in any type of liquid-liquid extraction technology. The cascade of co- or countercurrent mixing-decanting devices, centrifugal extractors, packed or plate columns and the like are examples.

The aqueous solution depleted of free acid may again be treated, as many times as desired, until a complete depletion of the ammonium hydroxide is obtained, if desired.

The organic phase is subjected to a treatment in order to isolate the HMTBS. This is preferably carried out by vaporization of the solvent or by an extraction with hot water. To avoid a possible deterioration of the HMTBA, the heat treatment can be maintained as low as possible by application of a vacuum.

In these two ammonium salt dissociation processes, an aqueous ammonium hydroxide solution is generated. The latter may be treated in order to concentrate the ammonium hydroxide. Distillation and concentration of the ammonium hydroxide in one or more stages with or without pressure will be preferred. A preliminary stripping stage may be envisaged. The concentrated ammonium hydroxide solution may be returned to the synthesis of the hydrocyanic acid which is involved in the synthesis of 2-hydroxy-4-methylthiobutyronitrile.

In a fifth stage, the aqueous solution of HMTBS and/or of free acid is concentrated. This is preferably carried out by evaporation of the water.

Figure 2:
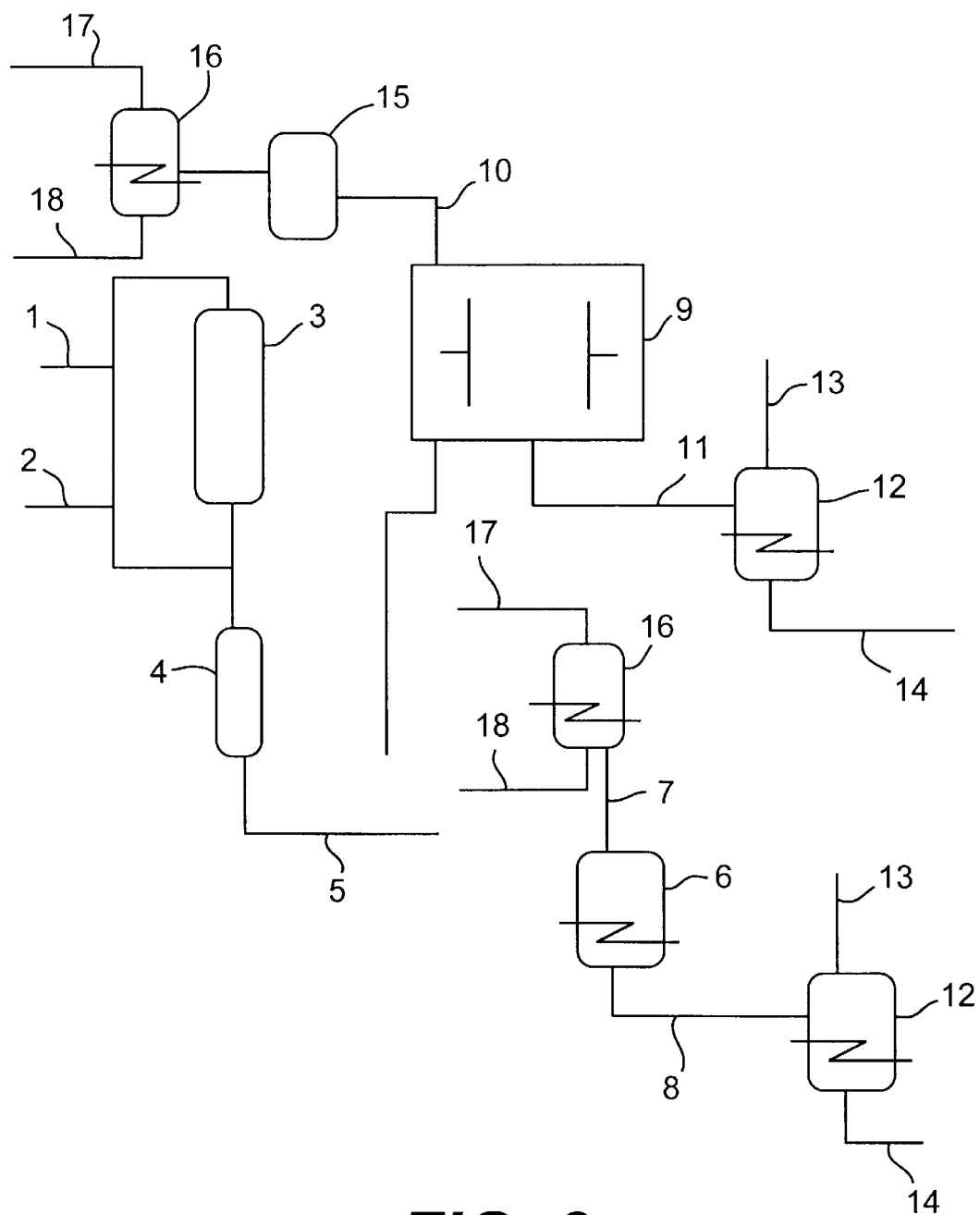
FIG. 2 is a schematic representation of a plant for carrying out the process according to the invention.

The subject of the invention is also a plant for carrying out the process according to the invention. Such a plant is schematically illustrated in FIG. 2 and comprises the conduits 1, 2 intended for introducing MTPA cyanhydrin and water, respectively, into the reactor 3. Reactor 3 is a fixed bed with recirculation which is packed with the immobilized enzymes or strains. Part of the solution is withdrawn from the reactor 3 and sent into a finishing reactor 4. The finishing reactor 4 is of the fixed bed type packed with the immobilized enzymes or strains. A concentrated HMTBS solution is then recovered at the outlet of reactor 4 via the conduit 5.

This concentrated HMTBS solution may be subjected to two completely independent treatments according to the type of final product desired.

If it is desired to recover a product containing a high proportion of HMTBS, the solution from the conduit 5 is conveyed into an evaporator 6 which makes it possible to concentrate the product and a concentrated solution composed mainly of HMTBS and containing a small quantity of free acid is recovered in conduit 8. The excess water as well as a fraction of the ammonium hydroxide are evacuated by conduit 7.

If it is desired to recover a product containing a high proportion of free acid, the concentrated HMTBS solution from conduit 5 is conveyed into a bipolar electrodialysis system 9. In this apparatus, the ammonium hydroxide is separated to a greater or lesser degree from the acid by electrodialysis. The mixture depleted of ammonium is recovered in conduit 11 and then concentrated in evaporator 12 in order to obtain a concentrated solution composed mainly of free acid and containing little or no HMTBS. The ammonium hydroxide-rich solution is withdrawn via conduit 10. The ammonium hydroxide is recovered by stripping 15.

This ammonium hydroxide effluent may be concentrated by distillation 16, the water is recovered in 18. The concentrated ammonium hydroxide solution 17 may be returned to the synthesis of HCN.

The following examples should be construed as illustrating the invention and not limiting it.

EXAMPLES

Example 1

Purification and N-terminal Sequencing of Nitrilase

The nitrilase was purified in four stages. The summary of the purification is given in Table 1.

The *Alcaligenes faecalis* cells were cultured for 24 hours, at 30° C., in a minimal medium in the presence of benzonitrile (0.5 g/l). After centrifugation of the culture, the pellet was taken up in TG buffer (25 mM Tris-HCl, 10% (w/v) glycerol, pH 7.5). The cellular suspension was treated with ultrasound and then centrifuged in order to obtain the crude extract. The crude extract was then treated with ammonium sulphate up to 30% saturation. The precipitate obtained was resuspended in TG buffer and then dialysed against 2 litres of the same buffer overnight. The solution obtained was then loaded onto a Q Sepharose Fast Flow HR 26/10 anion-exchange column previously equilibrated with TG buffer. The activity was then eluted with a gradient from 0 to 1 M NaCl. The active fractions were then loaded onto a Mono Q HR 5/5 anion-exchange column previously equilibrated with TG buffer. The nitrilase was eluted by means of a gradient from 0 to 1 M NaCl. To finish, the fractions containing the activity were combined, the ammonium sulphate concentration was then adjusted to 1 M. This solution was then loaded onto a phenyl Sepharose HR 5/5 hydrophobic interaction column previously equilibrated with TG buffer supplemented with 1 M (NH$_4$)$_2$SO$_4$. The activity was then eluted with a gradient from 1M to 0M of ammonium sulphate.

TABLE 1

Summary of the purification of nitrilase

| Fraction | Total protein (Mg) | Total activity (μMol/h) | Specific activity (μmole/h, mg) | Protein yield (%) | Purification factor |
|---|---|---|---|---|---|
| Whole cells | 955 | 4300 | 4.5 | 100 | 1 |
| Crude extract | | 2400 | | | |
| Ammo. sulphate | | 650 | | | |
| QSHL 26/10 | 3 | 360 | 120 | 0.3 | 27 |
| MonoQ HR 5/5 | 1.5 | 240 | 160 | 0.15 | 35 |
| Phenyl sepharose | 1 | 120 | 110 | 0.1 | 24 |

Operating Conditions:

[nitrile]=50 mM; Phosphate Buffer 100 mM pH 7.0; 30° C.

The molecular weight of the protein was determined by gel filtration. It was about 260 kDa. On an SDS-PAGE gel, a single band of 43 kDa was observed (95% purity). It was therefore probably α protein of $α_6$ structure with α weighing 43 kDa.

Example 2

Cloning of the *Alcaligenes faecalis* ATCC8750 Nitrilase

The $NH_2$-terminal sequence presented in Example 1 exhibited complete identity with the sequence of the N-terminal end of the *A. faecalis* JM3 nitrilase (Kobayashi et al., 1993, Proc. Natl. Acad. Sci. USA 90: 247–251), whereas the N-terminal ends of bacterial nitrilases exhibited 35 to 57% identity on 14 residues. The inventors hypothesized that the nitrilase of the invention purified from the ATCC8750 strain was similar to that described by Kobayashi et al. The cloning strategy then involved amplifying the gene for this nitrilase by a PCR reaction of the genomic DNA of the ATCC8750 strain with the aid of two nucleotide probes determined from the sequence given by Kobayashi et al.

The two probes were synthesized, one being capable of hybridizing with the 5' part of the sequence given by Kobayashi et al. and the other with the 3' part:

5' Part (PCRAF1): CCGGGAATTCATATGCAGACAA-GAAAAATCGTCC (Seq. ID No. 1)

3' Part (PCRAF2): TCCTTCTGCGTCCCCGATCCCG-CAT (Seq. ID No. 2)

Figure 3:
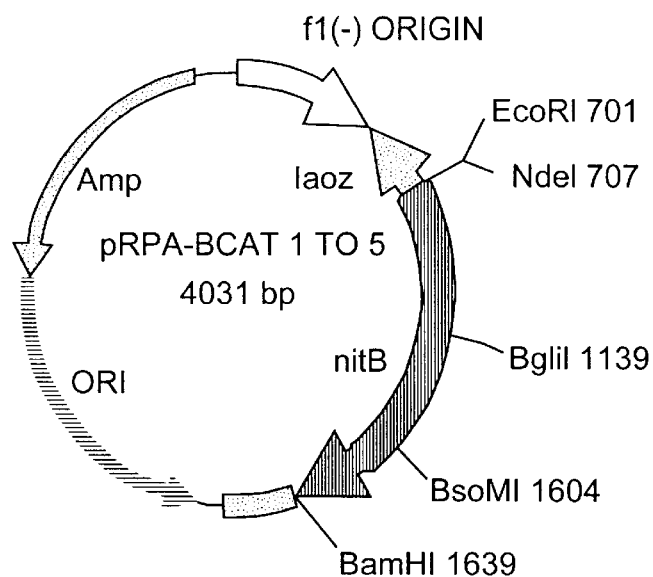
FIG. 3 represents the restriction map of the plasmids pRPA-BCAT1 to 5.

The primer PCRAF1 comprises 12 nucleotides in 5' which make it possible to introduce the restriction sites of the enzymes EcoRI and NdeI upstream of the ATG initiation codon. The primer PCRAF2 makes it possible to introduce the restriction site of the enzyme BamHI. The genomic DNA of the *A. faecalis* ATCC8750 strain was extracted according to the CTAB procedure described by Ausubel et al. (Current Protocols in Molecular Biology, John Willey & Sons Inc. Ed., 2.4.1–2.4.5) and 100 ng were used for each PCR reaction. In order to vary the specificity of amplification, various $MgCl_2$ concentrations were tested as indicated in Ausubel et al. in a total sample volume of 100 μl and with 2.5 units of Taq DNA polymerase (Perkin Elmer). Two additional reactions were carried out with 1.5 mM $MgCl_2$ and 5% DMSO or 5% formamide. A Perkin Elmer 9600 thermocycler was programmed with the following sequence: 5 min at 95° C., 30 cycles (30 sec at 95° C., 30 sec at 55° C., 45 sec at 72° C.) and 4 min at 72° C. The different amplification products were analysed on a 0.8% agarose gel. A predominant band, whose size corresponds to the expected size of 1.15 kb, was amplified in all the reactions but more specifically with 1.5 mM $MgCl_2$ and 5% DMSO. The reaction products under these conditions were therefore retained for subsequent stages. The sample was treated with proteinase K, ethanol-precipitated after a phenol-chloroform extraction. The pellet taken up in suspension was incubated for 2 h at 37° C. with 40 units of EcoRI enzyme and 40 units of BamHI enzyme. After running on a 0.7% agarose gel, the 1.15 kb band was cut out and extracted so as to be cloned into the vector pBSK⁻ (Stratagene, La Jolla, USA) opened by EcoRI-BamHI using conventional methods. Five independent clones, called pRPA-BCAT 1 to 5, were analyzed by enzymatic digestion of the plasmid DNA with the enzymes NdeI, EcoRI, BamHI, BspMI and BglII (as shown in FIG. 3). The pattern obtained corresponded to the theoretical restriction pattern for a plasmid obtained by this method with the sequence described by Kobayashi et al. The strain XL1Blue (pRPA-BCAT3) was deposited on Oct. 16, 1996 at The Centraalbureau Voor Schimmelcultures, Oosterstraat 1, P.O. Box 273, 3740 AG BAARN, Netherlands (CBS) under the number CBS 998–96.

Example 3

Sequencing of a 1130 bp Fragment Containing the DNA Encoding the Polypeptide Having the Nitrilase Activity.

Figure 4:
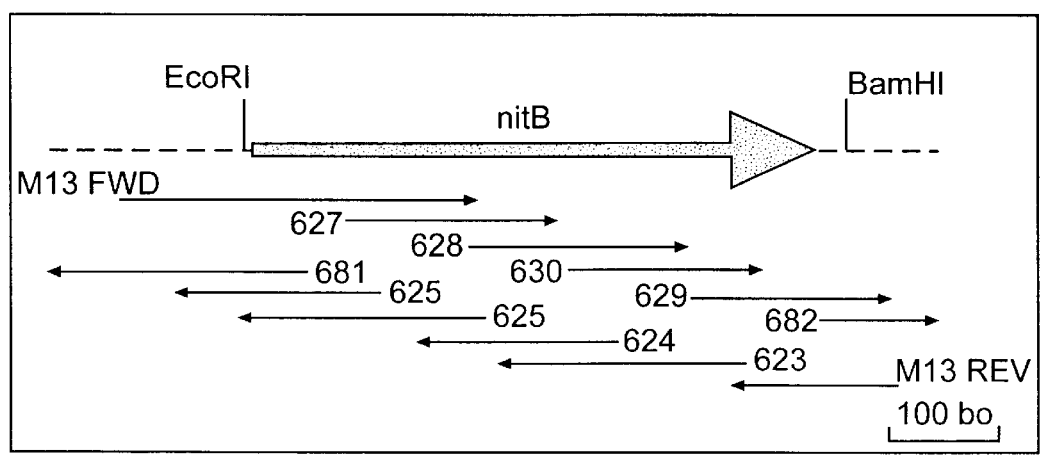
FIG. 4 represents the strategy for sequencing the fragment of 1130 bp containing the DNA sequence (called nitB in the Figure) encoding the polypeptide having the nitrilase activity according to the invention. The numbers refer to the identity of the primers used for the sequencing as well as the notations M13FWD and M13REV.

The insert cloned into the plasmid pRPA-BCAT3 was sequenced by the company Genome Express S.A. (Grenoble, France) using a DNA preparation produced in the laboratory (Wizzard Midi-prep kit, Promega). The strategy for sequencing this fragment, carried out according to conventional methods known to persons skilled in the art, is indicated in FIG. 4. The ten internal nucleotide primers (identified by the numbers 623 to 629 and 681 to 682 in FIG. 4) were synthesized based on the sequence of the *A. faecalis* JM3 nitrilase (Kobayashi et al.). This set was supplemented with the universal primers "Reverse" and "M12 Forward". Each region was read at least once on each DNA strand.

The DNA sequence obtained has two differences relative to the published sequence: one in the structure which is supposed to serve as transcription terminator and the other in the nitrilase gene, called nitB, leading to the substitution $Asn^{279}$→Asp. These two regions were then sequenced in the laboratory on the plasmids pRPA-BCAT1, 2, 4, 5 with two specific primers 710 and 682 (see FIG. 4). The C→T change at position 1412 (in accordance with the numbering by Kobayashi et al.) in the terminator was found in all the clones. This is a mutation which differentiates the two *A. faecalis* strains. The A→G change at position 1138 is present only in the plasmid pRPA-BCAT3. This is therefore a mutation introduced during the PCR by the Taq DNA polymerase.

Example 4

Expression of the Nitrilase in *E. Coli* BL21(DE3).

Figure 5:
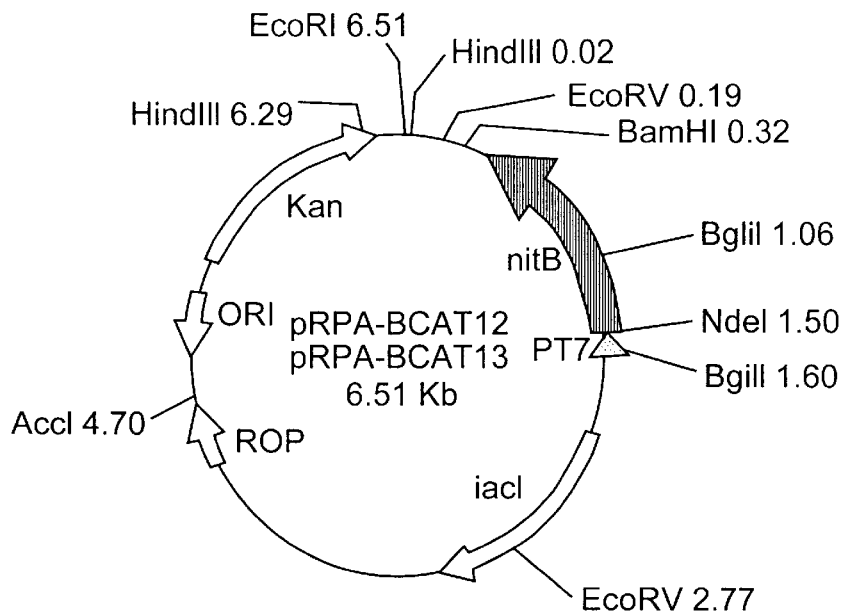
FIG. 5 represents the restriction map of the plasmids pRPA-BCAT12 and pRPA-BCAT13.

In order to confirm the identification of the DNA sequence cloned with the purified nitrilase gene, the nitB gene was placed under the control of the T7 phage (PT7) φ10 gene promoter according to the procedure described below: the 1.13 kb NdeI-BamHI inserts of the plasmids pRPA-BCAT3 and pRPA-BCAT4 were cloned into the vector pXL2432 to give respectively the vectors pRPA-BCAT12 and pRPA-BCAT 13 described in FIG. 5. The parent vector pXL2432 is a hybrid between the region of the plasmid pET9 (Studier et at., 1990, Methods in Enzymol. 185, 60–89), between the AccI and EcoRI sites, which includes the replication origin (ORI) and the selectable marker during the kanamycin (Kan) resistance, and the region between the EcoRI and AccI sites of the plasmid pET11a (Novagen Inc., Madison Wis., USA) which includes the expression cassette, the repressor gene lacI and the gene regulating copy number ROP.

Cultures were carried out under induction conditions according to the procedure below: the strain BL21(DE3) (Novagen Inc., Madison Wis., USA) containing the plasmid pRPA-BCAT12, the strain BL21(DE3) containing the plasmid pRPA-BCAT13 as well as the strain BL21(DE3) containing the plasmid pXL2432 were cultured for 16 h in LB medium at 37° C. (Miller, 1972, Experiments in Molecular Genetics—Cold Spring Harbor Laboratory, Cold Spring Harbor, N.Y.) containing 50 μg/ml of kanamycin, and then diluted 1/100 in the same medium and at the same temperature. When the cultures reached an $OD_{600}$ of between 0.5 and 1, IPTG, at the final concentration of 1 mM, was added. After culturing for 6 hours, the bacteria were collected. A similar procedure was adopted to culture the strain BL21 (DE3) containing the plasmids pRPA-BCAT12 and pXL2231, the strain BL21(DE3) containing the plasmids pRPA-BCAT13 and pXL2231 as well as the strain BL21 (DE3) containing the plasmids pXL2432 and pXL2231 by adding to the culture medium tetracycline in an amount of 12 μg/ml of medium. The plasmid pXL2231, which is derived from the vector pXL1635 (disclosed in Application No. FR 90/05185 of 24/04/1990), belongs to the IncP incompatability group and is therefore compatible with the plasmids pRPA-BCAT12 and 13 which possess the replication origin of the plasmid ColE1. Its selectable marker is tyetracycline resistance and it carries a 2.2 kb EcoRI-HindIII fragment containing the GroES and GroEL genes encoding the E. coli molecular chaperons (Fayet et a/., 1986, Mol. Gen. Genet. 202: 435–445). The expression of the nitrilase was analysed on a 10% SDS-PA gel in the crude fraction after sonication of the cells, and after centrifugation in the pellet and in the supernatant. The results are presented in FIG. 6 and show a high nitrilase (NitB) expression level in the extracts of cells in which at least one of the plasmids contains the nitB insert; however, this protein is essentially in insoluble form although the presence of the plasmid pXL2231 makes it possible to increase the quantity of nitrilase polypeptide in the soluble fraction.

Figure 6:
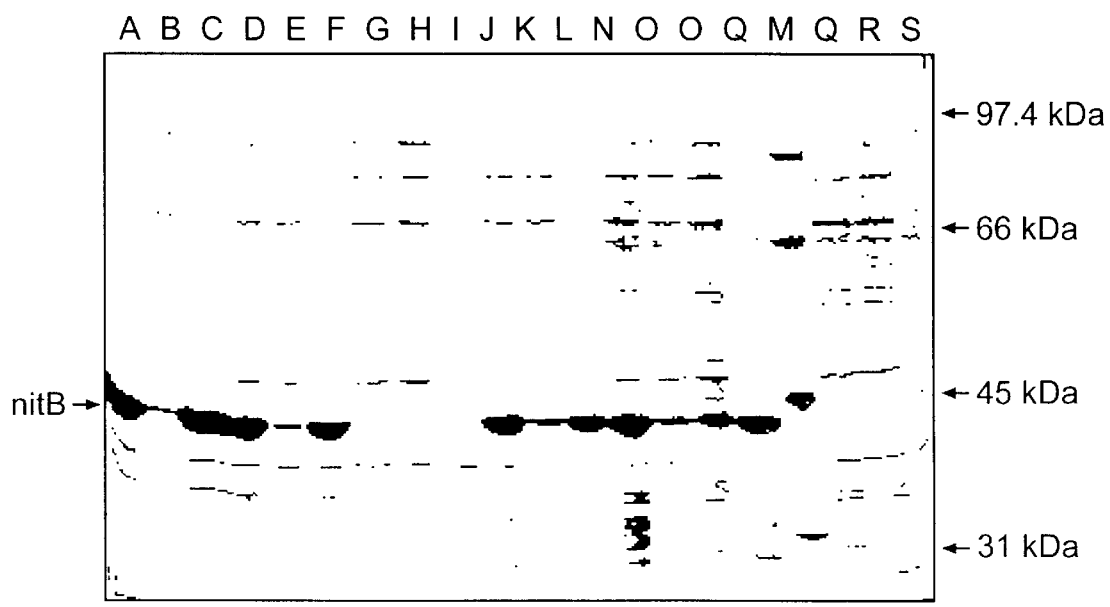
FIG. 6 represents electrophoresis on a 10% SDS-PAGE gel showing the expression of DNA sequences according to the invention in the *E. coli* strains BL21(DE3)/pRPA-BCAT12, BL21(DE3)/pRPA-BCAT13, BL21(DE3)/pRPA-BCAT12+pXL2231, BL21(DE3)/pRPA-BCAT13+pXL2231. Each lane corresponds to a quantity of 10 µg of soluble proteins and an equivalent volume of crude and insoluble fraction.

In FIG. 6, M represents the molecular weight marker; these are indicated in kDa. Moreover, the lanes have the meanings below:

A, D, G represent the crude fractions of BL21(DE3)+p/ RPA-BCAT12/RPA-BCAT13/XL2432, respectively;

B, E, H represent the supernatants obtained respectively from these same strains;

C, F, I represent the pellets obtained respectively from these same strains;

J, N, Q represent the crude fractions obtained respectively from BL21(DE3)+pXL2231+p/RPA-BCAT12/RPA-BCAT13/XL2432;

K, O, R represent the supernatants obtained respectively from these strains; and L, P, S represent the pellets obtained respectively from these strains.

The strain BL21(DE3)/pRPA-BCAT12+pXL2231 was called RPA-BIOCAT126. The strain BL21(DE3)/pRPA-BCAT13+pXL2231 was called RPA-BIOCAT127. The nitrilase activities of the cultures of RPA-BIOCAT126, RPA-BIOCAT127, and RPA-BIOCAT66 which corresponds to BL21(DE3)/pXL2432, were determined as follows: the cultures were carried out according to the procedure described above, with modification of the culture volume (50 ml) and the final concentration of IPTG (0.1 mM). The cultures were centrifuged and the cellular pellets taken up in 10 ml of 100 mM potassium phosphate buffer pH 7. The hydrolysis of HMTBN was carried out with 500 µl of this suspension added to 500 µl of 200 mM HMTBN solution pH7. A kinetic of hydrolysis was obtained by mixing 100 µl of this mixture with 900 µl of 0.1 N phosphoric acid at regular intervals for 1 to 4 hours. The quantities of HMTBA produced were analysed by HPLC as described in U.S. patent application Ser. No. 08/809,184 now U.S. Pat. No 5,814,497. The results are shown in Table 2.

TABLE 2

Activities of the strains RPA-BIOCAT66, 126 and 127

| RPA-BIO-CAT | MEDIUM | INDUCTION | CULTURE TIME | $OD_{660}$ | ACTIVITY (U) |
|---|---|---|---|---|---|
| 66 | LB Km | 0.1 mM IPTG | 24 h | 2.5 | 0 |
| 126 | LB Km Tc | 0.1 mM IPTG | 24 h | 2.4 | 15 |
| 127 | LB Km Tc | 0.1 mM IPTG | 24 h | 1.9 | 10 |

ABBREVIATIONS: Km: Kanamycin 50 µg/ml; Tc: tetracycline 12 µg/ml; h: hours; U: kg of HMTBA formed per hour and per kg of dry weight.

In order to enhance the solubilization of the nitrilase polypeptide expressed, the plasmid pRPA-BCAT37 was constructed as below. The plasmid pXL2391 was obtained by ligating the 5.9 kb EcoRI-PvuII fragment of the plasmid pDSK519 (Keen et al., 1988, Gene 70: 191–197), treated with Klenow polymerase, with the 2056 bp HindIII fragment extracted from the plasmid pHP45ΩSp (Prentki and Krisch, 1984, Gene 29: 303–313) treated with Mung Bean nuclease. The plasmid pXL2391 was then digested with SmaI and SacI and the 2.3 kb insert carrying the GroESL operon, extracted from the plasmid pXL2231 digested with HindIII, treated with Klenow and digested with SacI, was introduced therein. The plasmid pRPA-BCAT37 is therefore a derivative of the plasmid RSF1010 with a higher copy number than the plasmid pXL2231, compatible with the plasmids carrying the origin Co/E1 and carrying a marker for resistance to streptomycin. This plasmid was introduced into the strain BL21(DE3)/pRPA-BCAT12 to give the strain RPA-BIOCAT171. The activity of a culture carried out according to a procedure similar to that described above, but replacing the tetracyline with streptomycin at 100 µg/ml, was determined and is reported in Table 3.

TABLE 3

Activity of the strain RPA-BIOCAT171

| RPA-BIO-CAT | MEDIUM | INDUCTION | CULTURE TIME | $OD_{660}$ | ACTIVITY (U) |
|---|---|---|---|---|---|
| 171 | LB Km Sm | 0.1 mM IPTG | 24 h | 3.2 | 14 |

ABBREVIATIONS: Km: Kanamycin 50 µg/ml; Sm: Streptomycin 100 µg/ml; h: hours; U: kg of HMTBA formed per hour and per kg of dry weight.

Example 5

Expression of the Nitrilase in E. coli DH5alpha.

The plasmid pRPA-BCAT6 was constructed by cloning into pBCAT3 (See FIG. 3) the 0.6 kb ScaI-NdeI fragment of pXL2158 containing the Ptrp promoter and the ribosome-binding site RBScII (Levy-Schill et al., 1995, Gene 161: 15–20). The expression was performed with the strain DH5alpha containing the plasmid pRPA-BCAT6 and/or the plasmid pXL2035 (Levy-Schill et al.) with the following procedure: the preculture is incubated for 16 h at 37° C. in an M9 glucose medium (Miller, J.H. 1972. Experiments in Molecular Genetics. Cold Spring Harbor Laboratory, Cold Spring Harbor, N.Y.) containing 0.4% of casamino acids, 100 µg/ml of tryptophan, 100 µg/ml of carbenicillin. For the strains containing pXL2035, kanamycin was added in an amount of 50 mg/l. The expression occurred after a 1/100 dilution of the saturated culture in an identical medium but without tryptophan and incubation for 8 to 16 h at 37° C.

Figure 7:
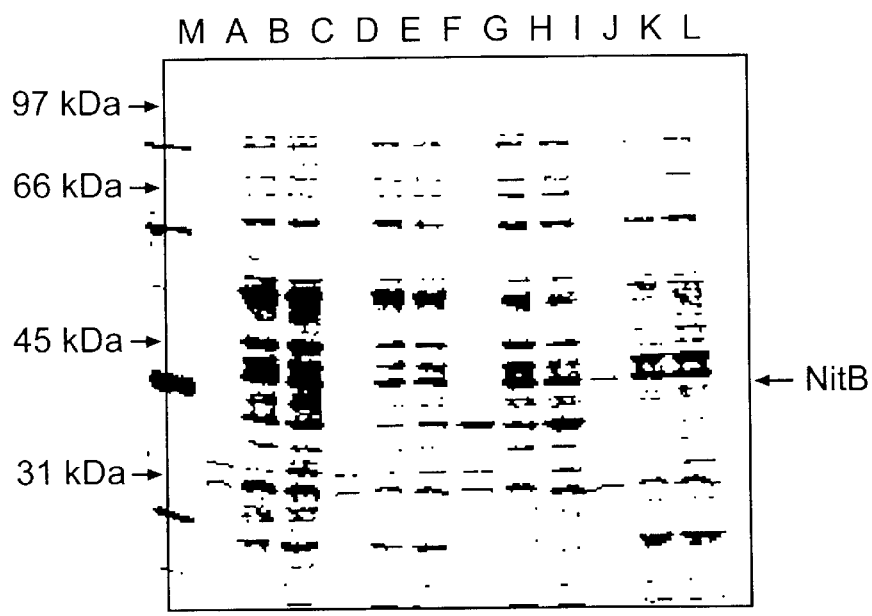
FIG. 7 represents electrophoresis on a 10% SDS-PAGE gel showing the expression of the reference DNA sequence according to the invention in the *E. coli* strains DH5α/pRPA-BCAT3, DH5α/pRPA-BCAT6, DH5α/pRPA-BCAT6+pXL2035, RPA-BIOCAT76. Each lane corresponds to a quantity of 10 µg of soluble proteins and an equivalent volume of crude and insoluble fraction.

SDS-PAGE analysis of the extracts of the different strains was performed as described in the preceding example and is represented in FIG. 7.

In this figure, M represents the molecular weight marker; these are indicated in kDa. Moreover, the lanes have the meanings below:

L, I, F, C represent the crude fractions obtained respectively from the strains DH5alpha+pRPA-BCAT/3,/6,/6+pXL2035, RPA-BIOCAT76;

K, H, E, B represent the supernatants obtained respectively from these same strains; and J, G, D, A represent the pellets obtained respectively from these same strains.

The plasmid pRPA-BCAT6 made it possible to obtain a small accumulation of a predominantly insoluble 43 kDa polypeptide. The coexpression of GroE from the plasmid pXL2035 reduced the overexpression, but after three successive subculturings of the strain DH5alpha (pRPA-BCAT6+pXL2035), the selected strain RPA-BIOCAT76 returned to an initial level of expression of the nitrilase polypeptide, the latter being practically completely soluble. The assays of activities of the cultures carried out according to the procedures described above and in the preceding example are presented in Table 4.

TABLE 4

Activity of the strains DH5alpha (pRPA-BCAT3), DH5alpha (pRPA-BCAT6), DH5alpha (pRPA-BCAT6 + pXL2035), RPA-BIOCAT76

| STRAIN | MEDIUM | CULTURE TIME | OD$_{660}$ | ACTIVITY (U) |
|---|---|---|---|---|
| DH5alpha (pRPA-BCAT3) | M9 Cb | 24 h | 4 | 0 |
| DH5alpha (pRPA-BCAT6) | M9 Cb | 24 h | 4 | 0.6 |
| DH5alpha (pRPA-BCAT6 + pXL2035) | M9 Cb Km | 24 h | 3 | 1.6 |
| RPA-BIOCAT76 | M9 Cb Km | 24 h | 3.8 | 5 |

ABBREVIATIONS: Km: Kanamycin 50 μg/ml; Cb: Carbenicillin 100 μg/ml; h: hours; U: kg of HMTBA formed per hour and per kg of dry weight.

These data show that the coexpression of GroE makes it possible to enhance the expression of the nitrilase and that a conventional strain selection by successive subculturing also contributes towards the enhancement of the activity of the recombinants.

Example 6
Expression of the Nitrilase in Pseudomonas putida and Alcaligenes faecalis.

Figure 8:
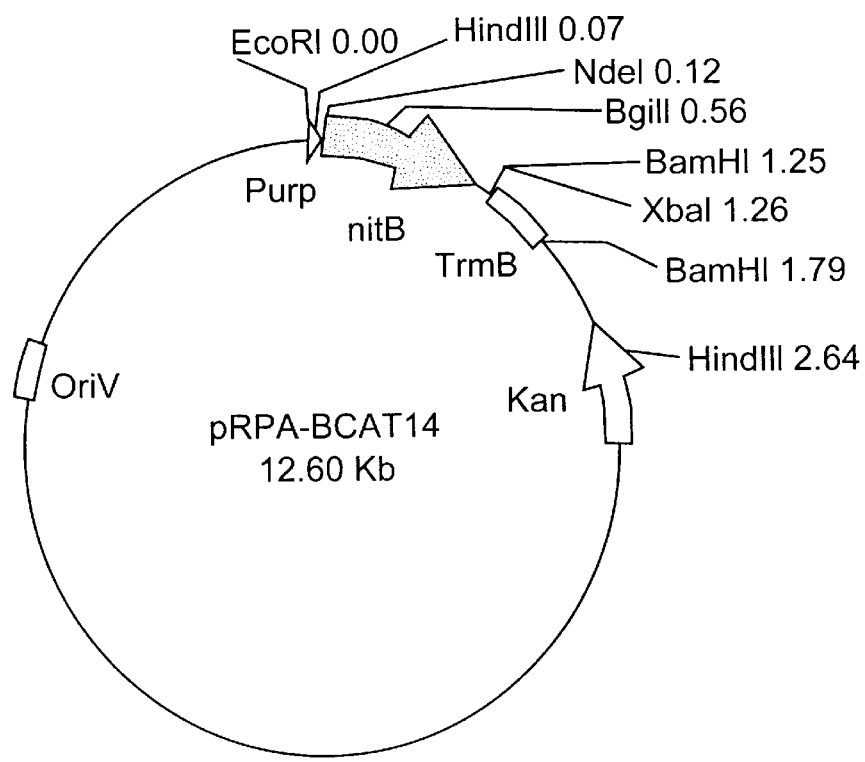
FIG. 8 represents the restriction map of the plasmid pRPA-BCAT14.

The expression system described in Example 5 was used to produce the nitrilase in Pseudomonas putida and A. faecalis. The 1.14 kb NdeI-XbaI fragment of pRPA-BCAT6 containing the nitB gene was introduced into the NdeI-XbaI sites of the vector pXL1289. The vector pXL1289 is a derivative of pKT230 (Bagdasarian et al., 1981, Gene 15: 237–247) carrying the multihost replication origin (oriV) in Gram-negative bacteria and which contains a 120 bp EcoRI-NdeI fragment carrying the P$_{trp}$ promoter and RBScII of pXL534 (Latta et al., 1990, DNA and Cell Biology, 9: 129–137), an NdeI-XbaI insert encoding the cobA gene (Crouzet a/., 1990, J. Bacteriol. 172: 5968–5979) and a 500 bp XbaI-BamHI insert containing the T$_{mmB}$ terminator of pXL534 (Latta et al., 1990, DNA and Cell Biology, 9: 129–137). The plasmid obtained pRPA-BCAT14 is therefore a derivative of pKT230 containing a gene which confers resistance to kanamycin (Kan) and the nitB gene under the control of Ptrp:RBScII (see FIG. 8).

During the introduction of this plasmid into the E. coli DH5alpha strain, a specific clone was selected: it expressed a nitrilase whose molecular weight on an SDS-PA gel was 44 kDa instead of 43 kDa. The plasmid harbored by this clone exhibited the same restriction pattern as pRPA-BCAT14 and was called pRPA-BCAT24. Finally, the plasmid pRPA-BCAT23 was constructed according to the same procedure as pRPA-BCAT14 with the following modification: the 136 bp StuI-BsmI fragment of pRPA-BCAT6 was replaced by the StuI-BsmI fragment of pRPA-BCAT4. The plasmid pRPA-BCAT23 therefore expressed a nitrilase NitB with an Asn residue at position 279.

The plasmids pRPA-BCAT14, 23 and 24 were introduced by electroporation into the Pseudomonas putida G2081 strain. The strain G2081 is derived from the strain KT2440 (Bagdasarian and Timmis, 1981, in Hofschneid and Goebel, Topics in Microbiology and Immunology, 47, Springer Verlag, Berlin) by selection of the spontaneous resistance to nalidixic acid and to rifampycin. The vector pKT230 was used as control plasmid.

The plasmids pRPA-BCAT14, pRPA-BCAT23, pRPA-BCAT24 and pKT230 were then extracted from the P. putida strains so as to be introduced by electroporation into the A. faecalis ATCC8750 strain (=RPA-BIOCAT1).

The strains G2081 (pRPA-BCAT14), G2081 (pRPA-BCAT23), G2081 (pRPA-BCAT24), G2081 (pKT230) with RPA-BIOCAT1 (pRPA-BCAT14), RPA-BIOCAT1 (pRPA-BCAT23), RPA-BIOCAT1 (pRPA-BCAT24), RPA-BIOCAT1 (pKT230) were cultured overnight at 30° C. in LB medium containing 50 mg/l of kanamycin. These pre-cultures were diluted 1/100 in M9 medium containing 50 mg/l of kanamycin and incubated for 20 h at 30° C.

Figure 9:
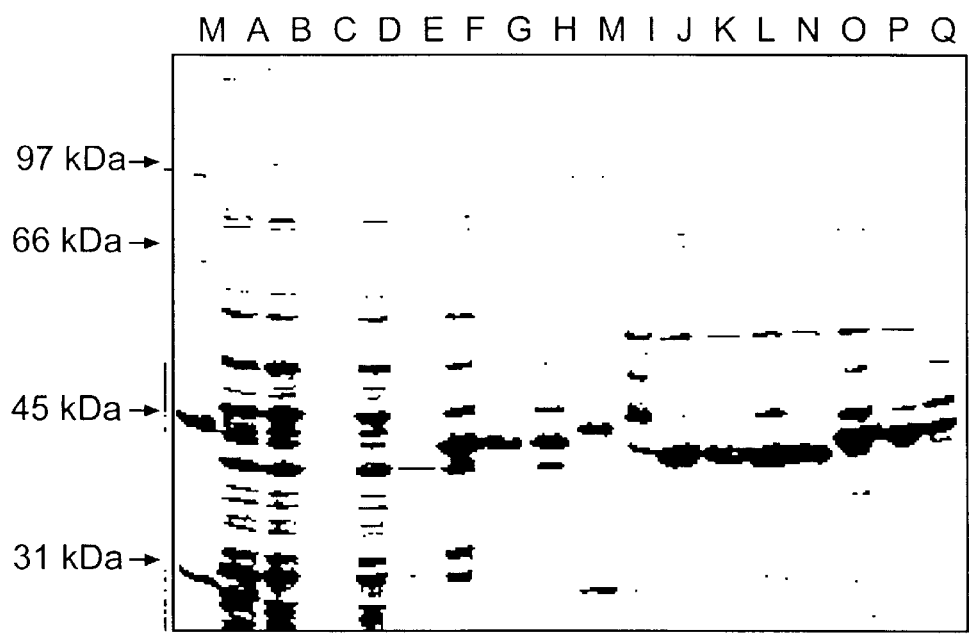
FIG. 9 represents electrophoresis on a 10% SDS-PA gel showing the expression of the DNA sequences according to the invention in the *P. putida* strains G2081 (pRPA-BCAT14), G2081 (pRPA-BCAT23), G2081 (pRPA-BCAT24), *A. faecalis* ATCC8750 (pRPA-BCAT14), *A. faecalis* ATCC8750 (pRPA-BCAT23), *A. faecalis* ATCC8750 (pRPA-BCAT24). Each lane corresponds to a quantity of 10 µg of soluble proteins and an equivalent volume of crude and possibly insoluble fraction.

The expression of the nitrilase was measured on a 10% SDS-PA gel in the crude fraction after sonication of the cells, after centrifugation in the pellet, and in the supernatant. The results are presented in FIG. 9. For the strains RPA-BIOCAT1 (pKT230) and G2081 (pKT230), only the crude extracts were loaded (lanes A and I respectively). In this figure, M represents the molecular weight marker; these are indicated in kDa. Moreover, the lanes have the meaning below:

B, D, F represent the crude fractions obtained respectively from the strains RPA-BIOCAT1 (pRPA-BCAT14), RPA-BIOCAT1 (pRPA-BCAT23), RPA-BIOCAT1 (pRPA-BCAT24);

C, E, G represent the supernatants obtained respectively from these same strains;

H represents the pellet obtained from RPA-BIOCAT1 (pRPA-BCAT24);

J, L, O represent the crude fractions obtained respectively from the strains G2081 (pRPA-BCAT14), G2081 (pRPA-BCAT23), G2081 (pRPA-BCAT24);

K, N, P represent the supernatants obtained respectively from these same strains; and Q represents the pellet obtained from G2081 (pRPA-BCAT24).

This experiment shows that the P. putida strains express large quantities of the three soluble nitrilase polypeptides and that only the nitrilase polypeptide at 44 kDa is overexpressed by the A. faecalis strain. The assays of activity of these cultures, carried out according to the procedure described in Example 4 show that the strains G2081 (pRPA-BCAT23), G2081 (pRPA-BCAT24), and RPA-BIOCAT1 (pRPA-BCAT24) have a nitrilase activity on HMTBN.

Example 7
Expression of the Nitrilase in Corynebacterium glutamicum.

The expression of the nitrilase was performed in the strain CGL1010 (=ATCC 14752) with the aid of the P cspB promoter (Peyret et al., 1993, Molecular Microbiol. 9: 97–109). A 530 bp fragment containing the P cspB promoter was amplified from the plasmid pCGL815 (Peyret et al.) with the aid of the following primers KS1 and KS2:

KS1: 5'-ACGCGTCGACCAGATCGTCAAGTTGTGG-3' (Seq. ID No. 3)

KS2: 5'-CATAGAGGCGAAGGCTCCTTG-3' (Seq. ID No. 4)

After digestion with SalI, the 530 bp fragment amplified was cloned into the plasmid pBSK (Statagene, La Jolla, USA) and opened by SalI and EcoRV to give the plasmid pCGL1084. An EcoNI/NdeI adaptor was prepared by hybridizing the following two oligonucleotides KS8 and KS9:

KS8: 5'-TCAAGGAGCCTTCGCCTCA-3' (Seq. ID No. 5)

KS9: 5'-TATGAGGCGAAGGCTCCTTG-3' (Seq. ID No. 6)

Figure 10:
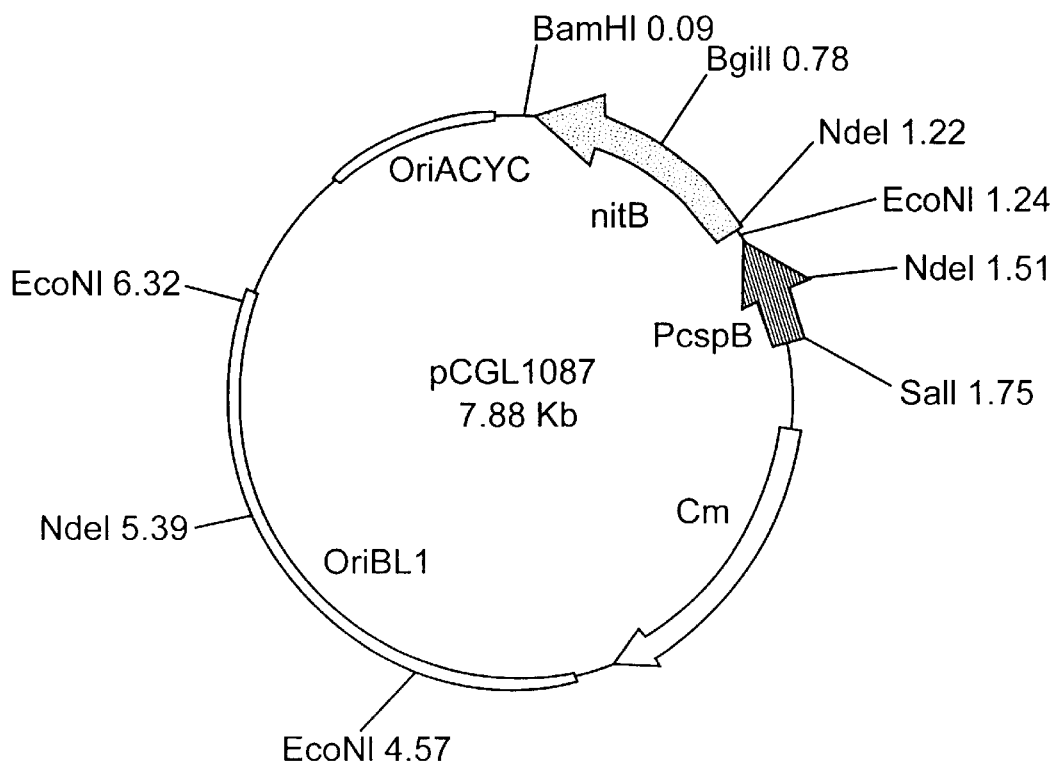
FIG. 10 represents the restriction map of the plasmid pCGL 1087.

The nitrilase gene was extracted from the plasmid pRPA-BCAT6 in the form of a 1.1 kb NdeI-XbaI fragment. It was introduced into pCGL1084 and opened with EcoNI and XbaI using the EcoI/NdeI adaptor described above to give the plasmid pCGL1086. The SalI-BamHI fragment of pCGL1086 containing PcspB::nitB was then cloned into the vector pCGL482 (Peyret et al.) at the SalI and BamHI sites, giving the plasmid pCGL1087. The plasmid pCGL1087 (See FIG. 10) is therefore a shuttle vector based on pBI1 (Santamaria et al., 1984, J. Gen. Microbiol. 130: 2237–2246) containing the replication origin of pACYC 184 recognized in *E. coli*, a gene conferring chloramphenicol (Cm) resistance and the PcspB::nitB fusion.

The plasmids pCGL1087 and pCGL482 were introduced by electroporation into CGL1010 as described by Bonnamy et al., 1990 (FEMS Microbiol. Lett. 66: 263–270). After culturing for 20 hours at 30° C. in a 3.7% Brain Heart Infusion medium (Difco Laboratories, Detroit, USA) supplemented with 5 mg/l of chloramphenicol, assays of nitrilase activities were carried out on culture samples as described in Example 4. The results show that the strain CGL1010 (pCGL1087) had nitrilase activity whereas the strain CGL1010 (pCGL482) had none.

Example 8
Expression of Nitrilase in *Streptomyces lividans*.

The expression of nitrilase was performed in the *S. lividans* TK24 strain (Hopwood et al., 1985, Genetic Manipulation of Streptomyces; A laboratory Manual, The John Innes Foundation, Norwich) with the aid of the plasmid pIJ6021 (Takano et al., 1995, Gene 166: 133–137) using the PtipA promoter (Holmes et al., 1993, EMBO J. 12: 3183–3191).

Figure 11:
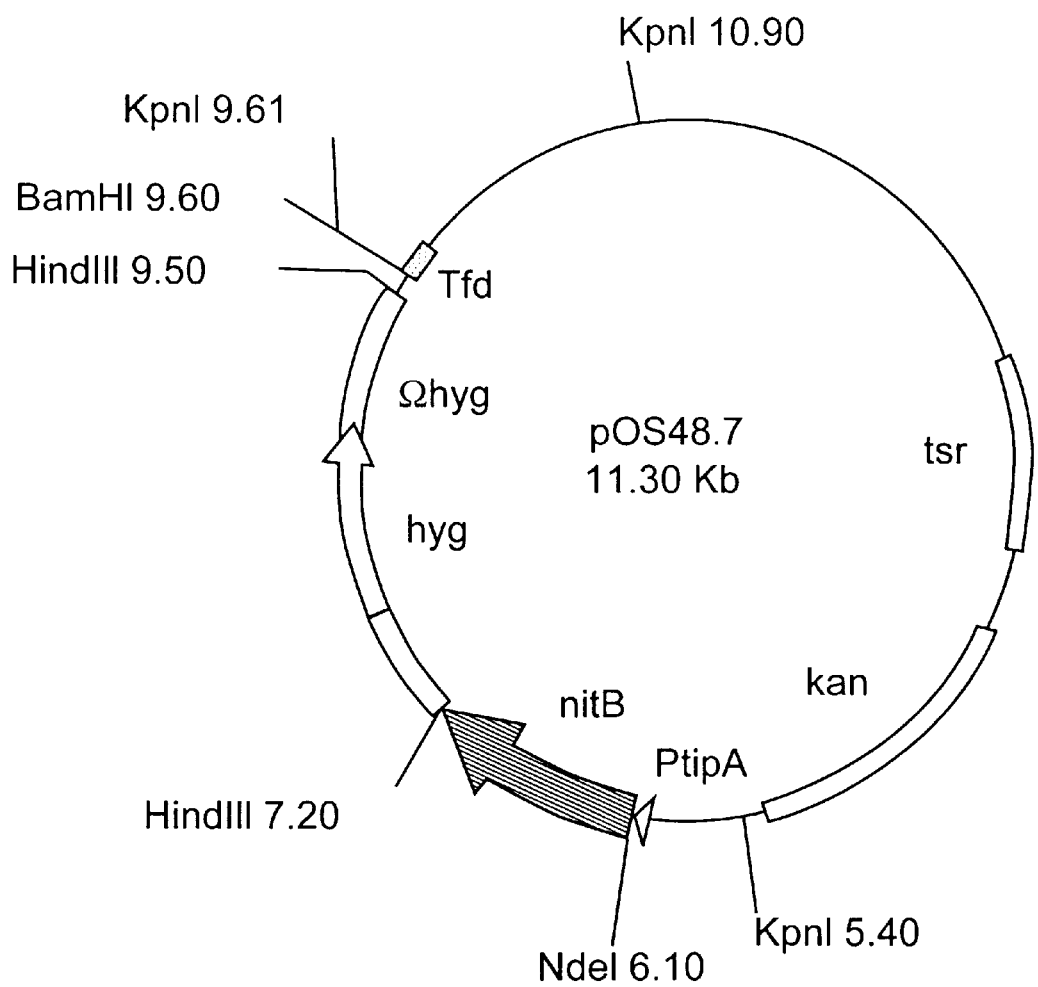
FIG. 11 represents the restriction map of the plasmid pOS48.7.

The plasmid pUC19 (Yanisch-Perron et al., 1985, Gene 33: 103–119) was modified by deleting the 140 bp TfiI fragment by TfiI digestion, treatment with Klenow, and self-ligation of the vector. The plasmid obtained was opened with EcoRI and BamHI so as to clone the 1.15 kb EcoRI-BamHI fragment of pRPA-BCAT3 containing the nitB gene. The plasmid pOS48.4 thus obtained had a unique TfiI site situated between the nitB gene and the BamHI site. This site was used to insert a 2.3 kb Ωhyg fragment extracted from the plasmid pHP45Ωhyg (Blondelet-Rouault et al., Gene, submitted) after digestion with BamHI and treatment with Klenow. The Ωhyg fragment contains the hygromycin phosphotransferase (hyg) gene of *Streptomyces hygroscopicus* (Zalacain et a/., 1986, Nucl. Acids Res., 14: 1565–1581) and confers hygromycin resistance on *S. lividans*. The plasmid pOS48.5 thus obtained was used to isolate a 3.45 kb NdeI-BamHI fragment containing the nitrilase gene followed by the hyg gene, which was cloned into the plasmid pIJ6021 (Takano et al.) opened with NdeI and BamHI. Given that the plasmid pIJ6021 replicates only in the Streptomyces, the ligation mixture was transformed in *S. lividans* TK24 by conventional methods (Hopwood et al.) by selecting the clones resistant to 200 mg/l of hygromycin (Boehringer Manheim). The plasmid DNAs of these clones were extracted by conventional methods (Hopwood et al.) and their restriction patterns indeed corresponded to the expected construct which was called pOS48.7 (see FIG. 11).

Two *S. lividans* strains containing pOS48.7 as well as a clone containing the plasmid pIJ6021 were cultured in 50 ml of TSB medium (Tryptic Soy Broth, Difco) at 30° C. for 72 h with a 5 mg/l kanamycin selection, and then thiostrepton was added at the concentration of 5 mg/l and the culture was continued for another 18 h according to the conditions described (Hopwood et a/.) The culture was harvested and the activity assay, carried out under the conditions described in Example 4, shows that the *S. lividans* TK24 strain (pOS48.7) expressed nitrilase activity contrary to the TK24 strain (pIJ6021).

Example 9
Hydrolysis of HMTBN with Other Nitrilases

The primary sequence of the *Comamonas testosteroni* sp., nitrilase described in Levy-Schil et al., 1995 exhibited 31% identity with the primary sequence of the nitrilase described in this invention. The recombinant strain of *E. Coli* TG1 (pXL2158, pXL2035), which expresses the *C. testosteroni* nitrilase, was cultured under the conditions described by Levy-Schil et al. and a cellular pellet was incubated in 100 mM phosphate buffer at pH 7 with 50 mM HMTBN, at 30° C. The measured activity was 2.3 kg/h.kg CS. Like the nitrilase of the invention, the *C. testosteroni* nitrilase is capable of hydrolysing HMTBN.

Furthermore, the data presented in Example 4 with the plasmids pBCAT12 and pBCAT13 show that the Asn279→Asp279 substitution on the *A. faecalis* ATCC8750 nitrilase makes it possible to conserve the activity on HMTBN.

Example 10
Supply of the Support 5 g of dry cells were added to 20 g of water adjusted to pH 7.0. The quantity of support (CELITE 545, Prolabo, France) indicated was then added and after a perfect homogenization, the suspension was cross-linked by addition of 15% glutaraldehyde based on the total dry mass followed by 10% polyethyleneimine (SEDIPUR, BASF, Germany). The suspension was stirred for 1 hour at room temperature.

The suspension was then flocculated by addition of 0.001% of an anionic flocculating agent, Superfloc A100. The cross-linked mass was recovered by filtration.

This mass was then again cross-linked by addition of 10% polyazetidine (KYMENE 557, Hercules, USA) based on the total dry mass. The mass, still wet, was then extruded through an orifice of 0.5 mm in diameter and dried.

The activity of the particles obtained was then determined according to the procedure described in U.S. patent application Ser. No. 08/809,184 now U.S. Pat. No 5,814, 497, incorporated by reference herein.

| g of support | activity (in %) |
|---|---|
| 0 | 100 |
| 2.5 g | 215 |
| 5 g | 250 |

The addition of a support for the cells considerably enhanced the activity.

The experiment was repeated by replacing the CELITE with wheat gluten (Roquette, France) partially soluble in water or gelatin (SBI, France) completely soluble in water.

| Support | % activity |
|---|---|
| 0 | 100 |
| 5 g of gluten | 160 |
| 5 g of gelatin | nd* |

*The cellular suspension does not flocculate and is not filterable.

This example shows that the gluten may be replaced by CELITE. On the other hand, if gelatin (completely soluble)

is added, the forming of the catalyst is impossible by the technique described above (extrusion).

Example 11

10 g of *Escherichia coli* BIOCAT171 of Example 4 prepared by aerobic culture in an Lb medium were mixed with 10 g of CLARCEL 78 (CECA, France) in 500 g of 100 mM phosphate buffer pH 7.0. After homogenization, 6 g of 25% glutaraldehyde were added and the suspension was stirred for 15 minutes at room temperature. 2 g of polyethylenimine were then added as well as 6 g of 25% glutaraldehyde. The whole was stirred for one hour at room temperature. The mixture was flocculated by the addition of 5 ml of a solution of SUPERFLOC A100 at 0.2% (CYTEC, France). The mass was filtered and the paste obtained was mixed with 16 g of polyazetidine at 12.5% (KYMENE 557, Hercules) and then extruded through an orifice of 0.5 mm in diameter. The vermicelli obtained were dried at 35° C. in an oven and then immersed for 30 minutes in a 1% $NaBH_4$ bath prepared in a 50 mM borate buffer pH 10.0. The biocatalyst was then washed with distilled water. The catalyst was stored at 5° C. or at room temperature in 500 mM phosphate buffer pH 8.0.

A thermostated column with an inner diameter of 3 cm and a height of 45 cm was filled with 100 g of biocatalyst. This column was connected to a pump via a recirculation loop. The total volume of the reactor was 430 ml. The loop was filled with a 25% solution of ammonium salt of hydroxymethylthiobutyric acid. The solution was fed through the top of the column downwards at an hourly flow rate of 20 I/h. The water which circulated in the jacket of the column and in the heat exchanger made it possible to maintain the temperature at 35° C. Demineralized water was added to the loop at a flow rate of 80 g/h and the 2-hydroxy-4-methylthio-butyronitrile at 20 g/h. The excess volume of the reaction medium was evaporated through the bottom of the column such that the volume of the loop remained constant. Thus, a continuous flow was obtained with a nitrile conversion rate of 95%. Furthermore, the concentration of the aqueous solution of ammonium salt of 2-hydroxy-4-methylthiobutyric acid obtained at the outlet of the reactor was 25%.

Example 12

The electrodialyzer used contained a stack of 9 cells with an active surface area of 2 $dm^2$, each of them composed of 2 compartments designed as follows:

salt/acid compartment: delimited on the cathode side by a cation-exchange membrane Neosepta CMB from Tokuyama Soda, and on the anode side by the cationic face of an Aqualytic bipolar membrane, and base compartment: delimited on the anode side by the cationic membrane, and on the cathode side by the anionic face of the bipolar membrane.

The anode was made of platinized titanium. The cathode was made of stainless steel.

The electrolyte contained an aqueous sodium sulphate solution having a conductivity of 100 mS/cm at 40° C. The circulation rate at the electrodes was 2×100 l/h. The volume was 5 l.

The "base" compartment was initially filled with 5 litres of a 1% ammonium sulphate solution.

The "salt/acid" compartment was initially filled with 5 litres of a solution at 1.44 mol/l of the ammonium salt of 2-hydroxy-4-(methylthio)butanoic acid.

The recirculation rate of the solutions was initially fixed at 130 l/h for the salt/acid compartment and at 190 l/h for the base compartment.

The electrodialysis was performed in a batch mode (operation with recirculation), at a mean temperature of 40° C. The intensity was set at 9A, that is to say a current density of 0.45 $kA/m^2$.

After 155 minutes of operation, the conductivity of the salt/acid compartment passed from 59 to 7.8 mS/cm.

The salvacid compartment contained 1.35 mol/l of 2-hydroxy-4-(methylthio)butanoic acid, at 100% in acid form.

The faradic yield was estimated at 71% and the energy consumption at 0.53 kWh per kg of acid formed.

Example 13

The electrodialyzer contained a stack of 8 cells with a configuration identical to that of Example 12.

The "base" compartment was initially filled with 5.27 litres of a 1% ammonium sulphate solution. The "salt/acid" compartment was initially filled with 4.85 litres of a solution at 1.39 mol/l of the ammonium salt of 2-hydroxy-4-(methylthio)butanoic acid.

The recirculation rate of the solutions was initially fixed at 60 l/h for the salt/acid compartment and at 150 l/h for the base compartment.

The electrodialysis was performed in a batch mode (operation with recirulation), at a mean temperature of 40° C. The intensity was set at 9A, that is to say a current density of 0.45 $kA/m^2$.

After 172 minutes of operation, the conductivity of the salt/acid compartment passed from 59 to 9.5 mS/cm.

The final volume of the salt/acid compartment was 4.67 litres.

The composition was comprised of:

| | |
|---|---|
| 2-hydroxy-4-(methylthio)butanoic acid: | 1.24 mol/l |
| ammonium 2-hydroxy-4-(methylthio)butanoate: | 0.148 mol/l |

The conversion rate was 86%. The final product was 89% in acid form.

The faradic yield was 74%. The energy consumption was estimated at 0.58 kWh per kg of acid formed.

Example 14

A device similar to that of Example 13 was used.

The "base" compartment was initially filled with 5.46 litres of a 1% ammonium sulphate solution.

The "salt/acid" compartment was initially filled with 5.23 litres of a solution at 1.24 mol/l of the ammonium salt of 2-hydroxy-4-(methylthio)butanoic acid.

The recirculation rate of the solutions was initially fixed at 90 I/h for the salt/acid compartment and at 150 I/h for the base compartment.

The electrodialysis was performed in a batch mode (operation with recirculation), at a mean temperature of 40° C. The intensity was set at 14 A, that is to say a current density of 0.7 $kA/m^2$.

After 105 minutes of operation, the conductivity of the salt/acid compartment passed from 57.6 to 9.8 mS/cm.

The final composition of the salt/acid compartment was the following:

| | |
|---|---|
| 2-hydroxy-4-(methylthio)butanoic acid: | 1.28 mol/l |
| ammonium 2-hydroxy-4-(methylthio)butanoate: | 0.14 mol/l |

The product was 90% in acid form.

Example 15

A device similar to that of Example 13 was used.

The trial was carried out with the content of the base compartment obtained at the end of Example 14.

The "salt/acid" compartment was initially filled with 5.2 litres of a solution at 1.44 mol/l of the ammonium salt of 2-hydroxy-4-(methylthio)butanoic acid.

The recirculation rate of the solutions was initially fixed at 50 l/h for the salt/acid compartment and at 150 l/h for the base compartment.

The electrodialysis was performed in a batch mode (operation with recirculation), at a mean temperature of 42° C. The intensity was set at 19 A, that is to say a current density of 0.95 kA/m$^2$.

After 53 minutes of operation, the conductivity of the salt/acid compartment passed from 59 to 27 mS/cm.

The final volume of the salt/acid compartment was 4.85 litres.

The composition was the following:

| | |
|---|---|
| 2-hydroxy-4-(methylthio)butanoic acid: | 0.87 mol/l |
| ammonium 2-hydroxy-4-(methylthio)butanoate: | 0.56 mol/l |

The conversion rate was 56%. The final product was 61% in acid form.

The faradic yield was 83%. The energy consumption was estimated at 0.7 kWh per kg of acid formed.

Example 16

200.1 g of HMTBS solution at about 1.5 M was concentrated batchwise in a rotary evaporator. The temperature of the bath was 45+/−5° C. The pressure was regulated at around 2.5×10$^3$ Pa (25 mbar). The temperature in the distiller varied from 25° C. at the start of distillation up to 40° C. at the end. After 3 hours, 41.9 g of a yellow viscous medium was recovered whose characteristics were the following:

| | |
|---|---|
| Viscosity at 25° C. (mm$^2$.s$^{-1}$) | 1150 |
| % HMTBA (Br/BrO3-) | 83.3 |

After adjusting the titre (dilution with H$_2$O), a product was obtained whose characteristics were the following:

| | |
|---|---|
| Viscosity at 25° C. (mm$^2$.s$^{-1}$) | 396 |
| % HMTBA (Br/BrO3-) | 79.5 |

The following mass distribution was obtained by potentiometry:

| | |
|---|---|
| % HMTBS | 81.6 |
| % HMTBA | 6.0 |

The ratio of the areas monomer or dimers/(monomer+dimers) was measured by HPLC

| | |
|---|---|
| monomer/(monomer + dimers) | 100 |
| dimers/(monomer + dimers) (*) | 0 |
| (*) no dimers were detected | |

Example 17

200.0 g of HMTBS solution at about 1.5 M was concentrated batchwise in a rotary evaporator. The temperature of the bath was 121/−5° C. The pressure was regulated at about 9.5×10$^4$ Pa. The temperature in the distiller varied from 100° C. at the start of distillation up to 113° C. at the end. After 3 hours, 41.5 g of a brown viscous medium were recovered whose characteristics were the following:

| | |
|---|---|
| Viscosity at 25° C. (mm$^2$.s$^{-1}$) | — |
| % HMTBA (Br/BrO3-) | 90.7 |

After adjusting the titre (dilution with H$_2$O ), a product was obtained whose characteristics was the following:

| | |
|---|---|
| Viscosity at 25° C. (mm$^2$.s$^{-1}$) | 117 |
| % HMTBA (Br/BrO3-) | 78.8 |

The following mass distribution was obtained by potentiometry:

| | |
|---|---|
| % HMTBS | 52.2 |
| % HMTBA | 28.7 |

The ratio of the areas monomer or dimers/(dimers+monomer) was measured by HPLC

| | |
|---|---|
| monomer/(monomer + dimers) | 95.0 |
| dimers/(monomer + dimers) | 5.0 |

Example 18

40.0 g of H$_2$O were added to 100.0 g of the medium described in Example No. 17. The medium was extracted with 75.0 g of isopropyl ether. After separation of the phases, 25.6 g of HMTBA, whose characteristics were the following, were recovered in the organic phase after evaporation:

| Determination | |
|---|---|
| Monomer/(monomer + dimers) (% area) | 97.0 |
| Dimers/(monomer + dimers) (% area) | 3.0 |
| Viscosity at 25° C. (mm$^2$.s$^{-1}$) | 55 |

Example 19: Aging of the solutions described in the preceding examples

| | Example No. 16 | Example No. 17 | Example No. 18 |
|---|---|---|---|
| Duration of storage at 25° C. | 40 d | 40 d | 100 d |
| Viscosity (mm$^2$.s$^{-1}$) | 387 | 116 | 66 |
| Monomer/(monomer + dimer) | 100.0 | 95.0 | 82 |
| Dimers/(monomer + dimers) | 0.0 | 5.0 | 18 |

The solutions of Examples 16 and 17 did not vary in their content of dimers after 40 days of storage.

What is claimed is:

1. A process for the continuous industrial scale preparation of 2-hydroxy-4-methylthiobutyric acid (HMTBA) or the ammonium salt of 2-hydroxy-4-methylthiobutyric acid (HMTBS) by enzymatic hydrolysis of 2-hydroxy-4-methylthiobutyronitrile, said process comprising:
   a) preparing a biological material having a nitrilase activity;
   b) immobilizing the biological material on a solid support, wherein the solid support has a particle size between 1 μm and 2 mm and is in an amount of 0.01 to 200% by weight of the biological material;
   c) contacting the immobilized biological material to 2-hydroxy-4-methylthiobutyronitrile to obtain the ammonium salt of 2-hydroxy-4-methylthiobutyric acid on an industrial scale; and
   d) optionally converting the ammonium salt obtained to the corresponding acid.

2. The process according to claim 1, wherein the nitrilase activity is obtained from an *Alcaligenes nitrilase.*

3. The process according to claim 2, wherein the *Alcaligenes nitrilase* is from *Alcaligenes faecalis.*

4. The process according to claim 1, wherein the nitrilase activity is obtained from genetic information encoding a nitrilase which is expressed in a host microorganism.

5. The process according to claim 4, wherein the host microorganism is *Escherichia coli* or a member of the genus Bacillus, Corynebacterium, Streptomyces, Saccharomyces, Kluyveromyces, Penicillium or Aspergillus.

6. The process according to claim 1, wherein the nitrilase activity is obtained from a nitrilase encoded by a gene cloned into a plasmid.

7. The process according to claim 6, when the plasmid is pRPA-BCAT3 deposited under the number CBS 998–96.

8. The process according to claim 1, wherein the nitrilase is coexpressed with a chaperon protein.

9. The process according to claim 8, wherein the chaperon protein is GroESL in *E. coli.*

10. The process according to claim 1, wherein the solid support is an ion-exchange resin, an alumina, a synthetic silica, a diatomaceous earth and silica gel, a zeolite, a charcoal, a partially water-soluble protein, or a polysaccharide.

11. The process according to claim 10, wherein the solid support is gluten.

12. The process according to claim 1, wherein at least one chemical agent is used to cross-link or insolubilize the biological material and the support.

13. The process according to claim 12, wherein the chemical agent is a polyazetidine polymer, a polyethyleneimine polymer, a polyamide polymer, an isocyanate polymer, an alginate gel, a k-carrageenan gel, an amine, an aldehyde, a carboxylic acid, or an isocyanate.

14. The process according to claim 13, wherein the biological material and the support are mixed in the presence of the chemical agent in order to obtain a paste which is extruded and then dried.

15. The process according to claim 12, wherein the biological material and at least one chemical agent are mixed and then deposited on the support in the form of a thin layer, wherein granules with a mean diameter of between 0.1 and 2 mm are obtained.

16. The process according to claim 1, wherein the particle size is between 100 μm and 2 mm.

17. The process according to claim 1, wherein the solid support is added in an amount of 10 to 100 wt %.

18. The process according to claim 1, further comprising concentrating the product obtained in step (c) or step (d).

19. A process for the preparation of a mixture of the ammonium salt of 2-hydroxy-4-methylthiobutyric acid (HMTBS) and 2-hydroxy-4-methylthiobutyric acid (HMTBA), wherein the mixture contains at least 60% HMTBA;

wherein the process comprises enzymatic hydrolysis of 2-hydroxy-4-methylthiobutyronitrile, said process comprising:

a) preparing a biological material having a nitrilase activity;

b) immobilizing the biological material on a solid support, wherein the solid support has a particle size between 1 μm and 2 mm and is in an amount of 0.01 to 200% by weight of the biological material;

c) contacting the immobilized biological material to 2-hydroxy-4-methylthiobutyronitrile to obtain the ammonium salt of 2-hydroxy-4-methylthiobutyric acid; and d) optionally converting the ammonium salt obtained to the corresponding acid by either electrolytically dissociating or heating the ammonium salt, whereby ammonium hydroxide is liberated.

20. The process according to claim 19, wherein the dissociation is carried out in an electrodialyzer with bipolar membranes having three compartments.

21. The process according to claim 19, wherein the dissociation is performed in an electrodialyzer with bipolar membranes having two compartments.

22. The process according to claim 19, wherein a mixture of HMTBS and HMTBA is obtained by heating the ammonium salt.

23. The process according to claim 19, wherein the liberated ammonium hydroxide is distilled, concentrated, and recycled in an HCN synthesis.

24. The process according to claim 19, wherein the mixture contains at least 80% HMTBA.

* * * * *

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
      (A) LENGTH: 34 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "probe"

(xi) SEQUENCE DESCRIPTION: SEQ ID NO:1:

CCGGGAATTC ATATGCAGAC AAGAAAAATC GTCC            34

(2) INFORMATION FOR SEQ ID NO:2:

(i) SEQUENCE CHARACTERISTICS:
      (A) LENGTH: 25 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "probe"

(xi) SEQUENCE DESCRIPTION: SEQ ID NO:2:

TCCTTCTGCG TCCCCGATCC CGCAT            25

(2) INFORMATION FOR SEQ ID NO:3:

(i) SEQUENCE CHARACTERISTICS:
      (A) LENGTH: 28 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "primer"

(xi) SEQUENCE DESCRIPTION: SEQ ID NO:3:

ACGCGTCGAC CAGATCGTCA AGTTGTGG            28

(2) INFORMATION FOR SEQ ID NO:4:

(i) SEQUENCE CHARACTERISTICS:
      (A) LENGTH: 21 base pairs
      (B) TYPE: nucleic acid
      (C) STRANDEDNESS: single

```
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:4:

CATAGAGGCG AAGGCTCCTT G                                              21

(2) INFORMATION FOR SEQ ID NO:5:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO:5:

TCAAGGAGCC TTCGCCTCA                                                 19

(2) INFORMATION FOR SEQ ID NO:6:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO:6:

TATGAGGCGA AGGCTCCTTG                                                20
```